United States Patent [19]

Tegtmeier

[11] Patent Number: 4,845,033
[45] Date of Patent: Jul. 4, 1989

[54] PROCESS FOR A CONTINUOUS FERMENTATIVE PRODUCTION OF LOW ALIPHATIC ALCOHOLS OR ORGANIC SOLVENTS

[75] Inventor: Uwe Tegtmeier, Braunschweig, Fed. Rep. of Germany

[73] Assignee: Starcosa GmbH, Braunschweig, Fed. Rep. of Germany

[21] Appl. No.: 254,464

[22] Filed: Oct. 6, 1988

[30] Foreign Application Priority Data

Oct. 9, 1987 [DE] Fed. Rep. of Germany ....... 3734124

[51] Int. Cl.$^4$ .......................... C12P 7/02; C12P 7/14
[52] U.S. Cl. .................................... 435/162; 435/157; 435/160; 435/161; 435/813
[58] Field of Search ............... 435/162, 161, 813, 160, 435/155

[56] References Cited

U.S. PATENT DOCUMENTS

| | | | |
|---|---|---|---|
| 4,451,566 | 5/1984 | Spencer | 435/813 |
| 4,460,687 | 7/1984 | Ehnstrom | 435/813 |
| 4,487,785 | 12/1984 | Epchtein | 435/813 |
| 4,680,263 | 7/1987 | Yamada et al. | 435/162 |
| 4,738,930 | 4/1988 | Faltejskek et al. | 435/162 |

FOREIGN PATENT DOCUMENTS

8501064 3/1985 European Pat. Off. .
0195094 9/1986 European Pat. Off. .

OTHER PUBLICATIONS

Biotechnology and Bioengineering, vol. XX, 1978, pp. 709-726, published by John Wiley & Sons, Inc., New York, U.S.A.; by A. Margaritis et al, entitled "The Rotorfermentor. I. Description of the Apparatus, Power Requirements, and Mass Transfer Characteristics".

Biotechnology and Bioengineering, vol. XX, 1978, pp. 727-753 and published by John Wiley & Sons, Inc., New York, U.S.A.: by A. Margaritis et al., entitled: "The Rotorfermenter. II. Application to Ethanol Fermentation".

The Yeasts, vol. II Technology of Yeasts; F. Reiff (Editor); Published by H. Carl, Nuernberg, Federal Republic of Germany; 1962; pp. 501-610.

*Primary Examiner*—Herbert J. Lilling
*Attorney, Agent, or Firm*—W. G. Fasse; D. H. Kane, Jr.

[57] ABSTRACT

Low aliphatic alcohols or organic solvents, especially ethanol are continuously produced by fermentation from sugar containing nutrient substrates. The process includes two fermentation steps or stages in which the substrate is subjected to the effects of microorganisms such as yeast. The first fermentation stage has a volume of 10 to 20% of that of the second fermentation stage. By adjusting the environmental conditions in each stage a large cell growth with a small portion of the total supplied substrate quantities takes place in the first activation stage and a high product formation rate is achieved with a considerably larger portion of the entire supplied substrate quantity in the second production stage. A partial outflow stream from the first stage is microfiltered and the permeate as well as the unfiltered outlet flow of the first stage, is directed into the second stage. The outlet flow of the second stage is microfiltered and the concentrate is partly discharged as a product output stream and partly returned to the second stage. The transfer flow and return flow streams and the discharge of the permeate and the product streams from the second stage are adjusted so that, for dwell times of the cell mass of up to two hours in the first stage and up to 15 hours in the second stage, an average cell age of 40 to 100 hours is achieved with a corresponding high yield output.

9 Claims, 1 Drawing Sheet

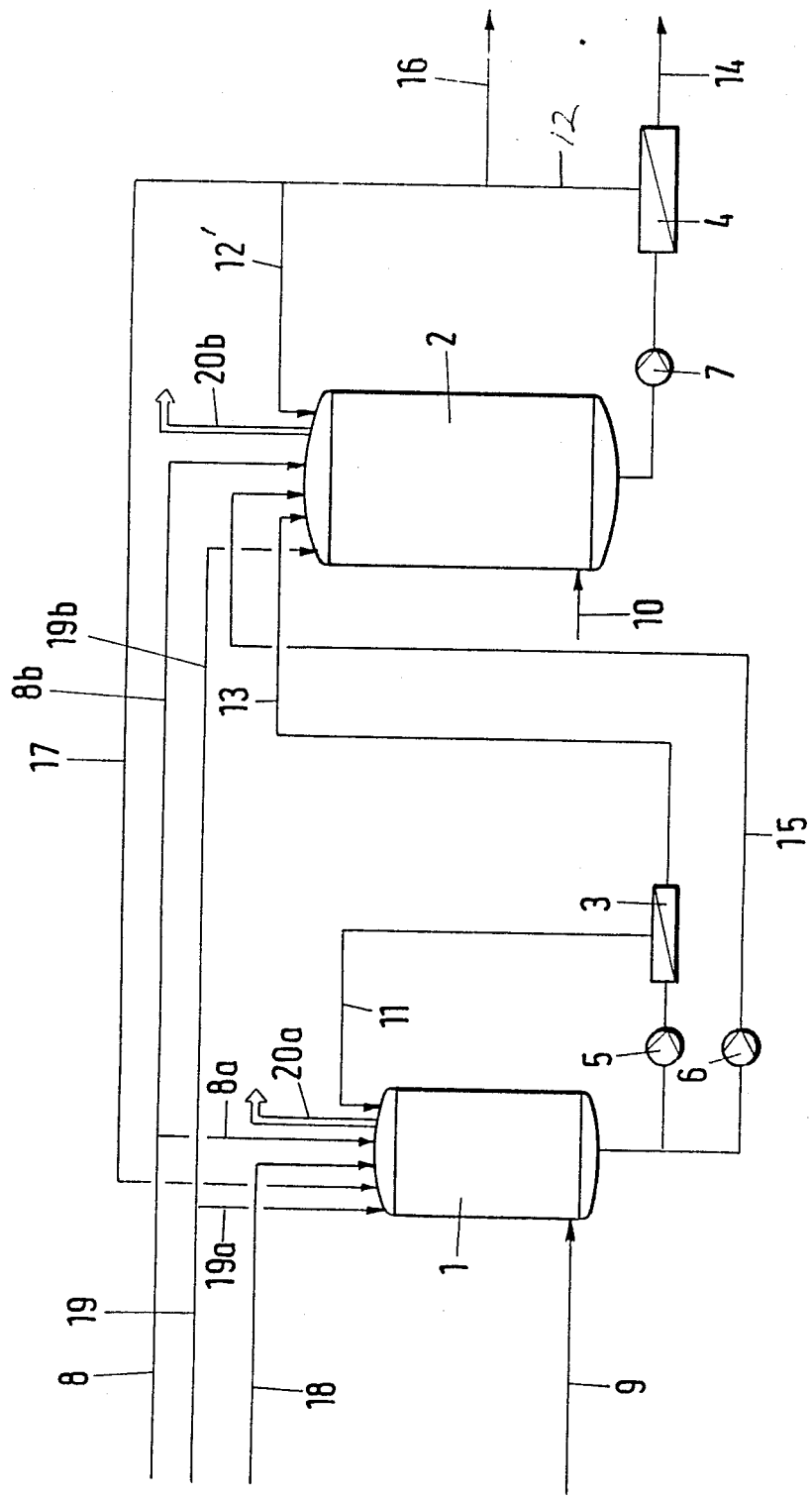

PROCESS FOR A CONTINUOUS FERMENTATIVE PRODUCTION OF LOW ALIPHATIC ALCOHOLS OR ORGANIC SOLVENTS

FIELD OF THE INVENTION

The invention relates to a process for a continuous fermentative production of low aliphatic alcohols or organic solvents, especially for producing ethanol from a sugar-containing substrate or nutrient medium, such as sugar beet molasses, whereby the substrate is subjected to the action of microorganisms, especially yeast, while the process is performed in an unsterile manner with two sequential fermentation steps.

DESCRIPTION OF THE PRIOR ART

European Patent Publication No. 0,195,094, published on Sept. 24, 1986 discloses a method for producing by a continuous fermentation, solvents, such as butanol, acetone, and especially ethanol. The material being fermented is an aqueous sugar or starch containing medium. Ethanol is produced as a metabolic product of yeasts and bacteria. The ethanol is separated out of the process by two material run-off streams each having a different composition. One stream (7) constitutes the permeate obtained by membrane filtration (2) and is substantially free of yeast and/or bacterial cells and solid particles. The other stream (8) is taken out directly from the fermentation fluid as a fermenter material stream. The other stream contains most of the non-soluble substances and the product forming biomass. The other stream (8) is kept smaller than the first stream (7). The known process achieves a high active cell concentration of the producing microorganism and a high production efficiency under non-sterile operating conditions. Yet, this known process leaves room for improvement, as will be described below.

PCT Patent Publication WO No. 85/01064 published on Mar. 14, 1985 is based on U.S. Ser. No. 526,437, (U.S. filling date is Aug. 25, 1983-Cheryan et al.) and discloses a continuous fermentation process for milk or whey products and by-products from which a substantial portion of the high molecular weight components has been removed. These starting materials are continuously introduced into an agitated fermenter. These materials also include one or more microorganisms capable of metabolizing lactose, glucose, or galactose for producing one or more metabolic products or low metabolic weight and carbon dioxide. A portion of the content of the fermenter is continuously passed through a filter for producing a permeate fraction and a concentrate fraction. The metabolic products are recovered from the permeate. The concentrate fraction is recycled into the fermenter.

The rotor fermenter I and II as described in "Biotechnology and Bioengineering", Vol. 20, pages 709 to 753, by A. Margaritis et al., John Wiley and Sons, Inc. (1978), is suitable for batch type and continuous operations. Details of the present invention are not shown in these references.

The fermentative production of low aliphatic alcohols and of organic solvents has become ever more important recently. Firstly, fermentative production processes are suggested due to the future dwindling of fossil fuels to provide a replacement for the fossil fuels based on renewable resources as, for example, especially through the production of ethanol, butanol, and acetone. Secondly, fermentative processes are capable of producing more stable alcohols for further chemical processing than can be produced from natural crude oil or petroleum. An example of this advantage is represented by 2,3-butanediol (2,3-butylene glycol) which cannot be economically obtained by chemical methods through catalytic dehydration.

Especially ethanol is a raw material for future use as a basic component of further chemical reactions as well as a liquid energy source which may, for example, be used as a fuel additive.

In the light of the advancing automation of the production processes, continuous methods of production are being called for more and more often. In view of the production of ethanol as well as other organic solvents and low aliphatic alcohols, fermentation represents the process step which is most widely still carried out intermittently or non-continuously. A continuous process for the fermentation step would make it possible to carry out the entire production in a continuous manner so that process monitoring control and production could be carried out more efficiently.

It is important for an effective further processing of these chemical compounds produced fermentatively, to achieve a high product concentration in the fermentation, so that the further process steps may be carried out with as small an energy expenditure as possible.

Furthermore, it is desirable that the continuous fermentation process is carried out in a stable manner, that is to say, that infections or contaminations of this biological process by microorganisms foreign to the process, is to be prevented as much as possible. In any event, the concentration of such foreign microorganisms must be held to a level low enough so that side reactions do not occur or that the formation of any undesirable secondary products does not disturb the desirable fermentation process.

Conventional continuous fermentation methods, especially those for producing ethanol, cannot achieve the above mentioned requirements. On the one hand, it is necessary in the known processes to carry out an in-line sterilization or a raw material sterilization in order to prevent infections or contaminations by foreign microorganisms. Such sterilizations are energy consuming. On the other hand, the biomass concentrations which are necessary for a microbiologically stable process operation cannot be achieved in the conventional processes because the routing or directing of the biomass in known processes requires a separation step by means of a separator or microfilter. The latter known processes which operate with biomass separation through a separator fail completely when bacteria are used as the production microorganism.

The continuous fermentation process disclosed in the above mentioned European Patent Publication No. 0,195,094 must operate with appropriately high cell concentrations. For this purpose membranes must be used instead of separators for increasing the internal cell concentration and cell retention. In this reference a fermenter is used operating in the manner of a membrane reactor. A biomass concentration is adjusted in the fermenter which achieves an essentially stable process operation due to the substrate competition relative to foreign microorganisms.

However, the just described known method can be improved especially with regard to processes which are to result in a high end product concentration and hence are subject to high stress conditions for the operating microorganism. Under such production conditions it is not possible to achieve a sufficient activation of the biomass not to maintain the activity of the microorganisms over long periods of time in a system consisting of a single fermenter as disclosed in said European Patent Publication No. 0,195,094.

OBJECTS OF THE INVENTION

In view of the foregoing it is the aim of the invention to achieve the following objects singly or in combination:

to provide a process for continuously fermentatively producing low aliphatic alcohols or organic solvents, especially ethanol in an efficient and inexpensive manner;

to maintain, in such a process, a high active cell concentration of the producing microorganism;

to achieve a high final product concentration in such a process;

to maintain a high activity of the producing microorganisms over long periods of time for a continuous operation in such a process;

to achieve a high productivity and therewith a high product output rate in such a process; and to carry out such a process in an unsterile or non-sterile manner, that is to say, in a manner which does not require energy costly in-line sterilization or raw material sterilization in order to prevent infections and to avoid disruption of the fermentation process even while operating in a non-sterile manner.

SUMMARY OF THE INVENTION

The above objects have been achieved in a process for the continuous fermentative production of low aliphatic alcohols or organic solvents according to the invention, wherein two separate fermentation steps are performed, namely an activation step or stage for inducing a large cell growth or cell activation and a second fermentation step or stage for producing a final product with a high product formation rate with a volume ratio of the first stage to the second stage of between 1:10 and 1:5. Furthermore 5 to 20% of the entire substrate or raw material quantity is introduced into the first stage and 80 to 95% of the total substrate or raw material quantity is introduced into the second stage. A gas, such as oxygen, is introduced into both stages but the first stage receives a multiple of the amount of gas introduced into the second stage so as to establish an oxygen partial pressure in the first stage of approximately 3% and an oxygen partial pressure in the second stage of approximately 1%. The temperature of the first stage is regulated or adjusted at 30° to 35° C. and the temperature of the second stage is regulated at 35° to 40° C. A partial output flow from the first stage is subjected to microfiltration, whereupon the permeate stream as well as the outlet drain stream from the first stage is supplied into the second stage. The outlet flow of the second stage is subjected to a microfiltration, whereby the permeate stream is carried away as an output stream and the concentrate stream is partially discharged as the product stream and partially directed back into the second fermentation stage. The transfer streams from the first to the second stage as well as the return stream of the partial flow of the concentrate and the withdrawing of the permeate and the product output stream from the second stage are adjusted so that for dwell times of the cellular substance of about 0.5 to 2 hours in the first stage and of about 5 to 15 hours in the second stage, an average cell age of about 40 to about 100 hours is achieved and maintained.

The process according to the invention allows the average cell age of the microorganism population to be adjusted to be relatively high, whereby losses of the biomass can be reduced. This leads to a corresponding reduction in losses in yield or output.

The activation or first stage is operated in such a manner that on the one hand high growth rates or activation rates of the producing microorganism are achieved. On the other hand the environmental conditions are very unfavorable for foreign microorganisms which is an advantage, because especially in the production of ethanol by yeast fermentation the over growth of foreign yeast can be prevented simply by controlling the operating parameters. In this context the osmotic pressure of the medium is an important cell activity criterium. Ethanol producing yeasts are more tolerant to ethanol than are pure growth yeasts. By directing a stream of the medium from the activation stage into the production stage, a highly active microorganism flow having a low cell age is continuously added to the production stage. This feature of the invention makes sure that the medium conditions in the production stage can be selected or adjusted in such a manner that greatly stressful conditions for osmo-sensitive and ethanol-sensitive microorganisms are established without significantly limiting the activity of the producing biomass. Hence, a constantly high biomass concentration can be maintained in the production stage over a long working or processing time. Another advantage is seen in that it is now possible to increase the average dwell time of the cells which leads to a higher product yield or output.

Microfiltration modules are provided for discharging the permeate streams of which the flow volumes can be regulated to adjust the environmental conditions in the activation stage and in the production stage. In order to achieve the best possible operating results, it is advantageous to use hollow fiber microfiltration modules. When other types of filtration modules are used, either the production costs rise sharply due to an increased concentrate stream, or unallowable shearing gradients arise when the medium penetrates or flows through the membranes of, for example a wrapped or rolled module, whereby mechanical damage of the biomass occurs.

By adjusting the outflow from the production stage, the content of total dry solids in the system can be limited and the appropriate volume of a biomass stream is removed from the system for adjusting or setting the average cell age. This outlet stream or outflow contains all the components which are non-soluble ingredients of the medium because of their particle size which lies above the maximum pore size of the microfiltration membranes. These non-soluble components, especially include flocculated protein components of autolized cells, and polysacchrides.

According to the invention it is especially advantageous to return a partial stream of the concentrate from the production stage back to the activation stage, whereby the biomass containing stream flowing from the activation stage into the production stage is similarly increased to maintain a volume flow balance. This feature assures that the total dwell time, or residence time of the biomass in the production stage is shortened and in the interim period or in intervals during reduced stress conditions in the activation stage the biomass undergoes an activation of its respiratory enzymes. In this manner the ATP (adenosine triphosphate) content of the cells is increased.

This type of operation of the process may be advantageously applied if microorganisms having a very low growth rate are to be used under the above described stress conditions in the production stage.

Furthermore, it is advantageous if the microorganism concentration in the first or activation stage is less than 80 g of dry solids per liter and the microorganism concentration in the second or production stage is more than 80 g of dry solids per liter.

BRIEF DESCRIPTION OF THE DRAWINGS

In order that the invention may be clearly understood, it will now be described, by way of example, with reference to the accompanying drawing, wherein the single FIGURE is a schematic diagram of the essential components and a flow diagram of the process flows for carrying out the method of the invention.

DETAILED DESCRIPTION OF THE PREFERRED EXAMPLE EMBODIMENTS AND OF THE BEST MODE OF THE INVENTION

As shown in the schematic diagram of the FIGURE, a first fermentation tank represents the activation stage 1 and a second fermentation tank represents the production stage 2. A common raw material or substrate supply conduit 8 is divided into a branch supply conduit 8a to provide substrate to the activation stage 1 and into a branch supply conduit 8b to supply the same substrate material to the production stage 2. The substrate or raw material may, e.g., be sugar beet molasses. Another supply conduit 18 provides further necessary nutrient and growth materials only to the activation stage 1. Both fermentation tanks 1 and 2 are supplied with an oxygen providing gas flow through a conduit 9 to the activation stage 1 and a conduit 10 to the production stage 2. The nutrient and growth materials comprise, e.g., A pump 5 pumps an outflow stream from the activation stage 1 to a microfiltration module 3 to provide a concentrate stream 11 of medium which does not pass through the filter module 3 and a permeate stream 13 of medium which does pass through the filter module 3. The concentrate stream 11 is directed back into the activation stage 1 while the permeate stream 13 is directed into the production stage 2. A pump 6 pumps a biomass containing outlet flow 15 from the activation stage 1 to the production stage 2.

Medium is pumped from the production stage 2 by a pump 7 through a microfiltration module 4, whereby the permeate stream 14 is discharged from the system as an output flow and a portion 12' of the concentrate stream 12 is returned to the activation stage 2. Another portion or partial stream 16 of the concentrate stream 12 is discharged from the system as a biomass containing output stream of the production stage 2. A further portion of the concentrate stream 12 is returned at 17 to the activating stage 1. The amount of medium discharged in the permeate stream 14 is largely dependent upon the final product concentration to be achieved.

In order to equalize the working volumes of the fermenting tanks 1 and 2, process water is supplied to the common water supply conduit 19 which separates into a branch supply conduit 19a for the activation stage 1 and a branch supply conduit 19b for the production stage 2.

The unused components of the gaseous medium supplied through conduits 9 and 10 for supplying oxygen to the activating stage 1 and production stage 2 respectively, as well as the generated reduction equivalent quantities of $CO_2$ exit the fermentation tanks 1 and 2 through gas vent conduits 20a and 20b respectively.

In the example embodiment shown in the Figure a portion or partial stream 17 of the biomass containing concentrate stream 12 discharged from the production stage 2 is fed back into the activation stage 1.

The invention will now be described in detail by way of two specific examples.

EXAMPLE 1

This example describes the continuous fermentative production of ethanol.

Starting from a pure microorganism culture, the product forming biomass was cultured in the two fermentation tanks 1 and 2, whereby the activation stage fermenter 1 was put into operation approximately 20 hours after the production stage fermenter 2. A commonly available baking yeast was used as the microorganism stock. The culture growth continued until the desired biomass concentration was reached and was carried out in the shortest possible time under optimal growing conditions, namely medium conditions corresponding to a temperature of 30° C., pH value of 4.8, soluble non-sugar dry solids of 4.0%, oxygen partial pressure of 2%, and a sufficient supply of nutrient and grow substances for achieving a high growth rate. The quantities of nutrient and growth substances were as follows:

VITAMIN REQUIREMENTS FOR 1 KG OF YDS 20 mg (Thiamine)
20 mg (Riboflavine)
100 mg (Pantothenic acid)
200 mg (Nicotine acid)
10–20 mg (Pyridoxine)
2–3 mg (Biotine)
1000 mg (m-inosit)

NUTRIENT AND GROWTH SUBSTANCES 20 g (potassium)
2 g (magnesium)
0.35 g (calcium)
1 g (sodium)
0.05 g (iron)
7.5 mg (copper)
19.5 mg (manganese)
4 mg (cobalt)
185 mg (zinc)
80 g (nitrogen)
30 g (phosphate)
10 g (sulphur).

Sugar beet molasses was used as the raw material or substrate.

The amount of substrate or molasses provided to each fermenter was adjusted or set so that the simultaneous formation of ethanol was induced through providing an excess of the usable C (carbon) source.

The medium conditions and the final alcohol concentration were adjusted to approximately 2 volume % by discharging appropriate amounts of permeate streams from the filter modules 3 and 4. The filter modules were equipped with hollow fiber microfilter modules from the manufacturer Enka AG, 5600 Wuppertal, Federal Republic of Germany, whereby the filter module 3 was of the type Md 080 TP 2L and the filter module 4 was of the type Md 150 CP 2N.

Starting with approximately 200 g of yeast dry solids (YDS) of the pure culture in the activation stage 1 with a working volume of 80 liters, and approximately 400 g of yeast dry solids of the pure culture in the production stage 2 with a working volume of approximately 400 liters, the desired concentration of biomass of approximately 50 g YDS per liter in the activation stage 1 was achieved after approximately 30 hours and the desired concentration of 110 g per liter in the production stage 2 was achieved after approximately 50 hours. Due to a linearly adjusted growth rate, the average cell age of the population amounted to approximately 30 to 35 hours at this point in time.

Next, all the system parameters were adjusted or set so that the fermentation plant could be operated with a maximum productivity and substrate yield with a high product concentration.

A sufficient cell activity was to be expected with an average cell age of approximately 65 hours. The average cell age is adjustable by appropriately selecting the magnitude of the biomass containing output flow 16 from the production stage 2 and is a reciprocal of the average dwell time or residence time of the biomass for a constant biomass concentration because for a continuous operation of a chemically static system, the growth rate in liter per hour (l/h) corresponds to the throughput rate D·(l/h), that is, to the average dwell period or residence time.

The conditions existing in the production stage 2 are extremely stressful conditions for the yeast so that no mentionable growth occurs. The cell mass removed from the production stage 2 in the biomass containing output flow 16 was replaced by cell mass provided by the biomass containing stream 15 from the activating stage 1 to the production stage 2.

In order that growth of the microorganisms, namely the yeast occurs in the activation stage 1, and in order that product formation or fermentative production of ethanol occurs in the production stage 2, the medium conditions of the two fermenter tanks 1 and 2 must be selected differently.

The product concentration and actually also the medium conditions are essentially prescribed by the selection of the magnitude of the permeate streams 13 and 14, whereby the permeate stream 14 as well as the biomass containing output flow 16 represent the product containing output streams of the process.

The oxygen necessary for the fermentation was provided by air supplied into the fermentation tanks at 9 and 10, whereby the air quantities were regulated depending on the actual oxygen partial pressures, whereby these air quantities were variable in accordance with the respective mass transport conditions.

The sugar beet molasses had a total content of fermentable sugar of 40 wt. % and impurities or foreign components in typical quantities.

Growth and nutrient substances were added only through the conduit 18 into the activation stage 1 in dosed quantities typical in the baker's yeast production.

The quantity of process water which was provided to both fermenters through the conduits 19a and 19b respectively, was a resultant quantity which was not directly determined, since the filling level control in both fermenter stages was done with the aid of the process water quantity. The water quantities were not directly determined but can be ascertained by balance calculations.

The exhaust gas quantities which exit through the gas outlet conduits 20a and 20b include the superfluous quantities of supplied gasing medium as well as the respective reduction equivalent $CO_2$ quantities. These exhaust gas flows were similarly not determined or measured, but were simply estimated with sufficient accuracy for calculating the yield with respect to the produced quantity of alcohol product.

All the important selectable material stream flows and process parameters are given in Table 1-1. The medium conditions and process parameters which are automatically adjusted to equilibrium conditions are given in Table 1-2. The method quantities or process parameters important for evaluating the process which may be calculated from the measured or adjusted quantities shown in Tables 1-1 and 1-2, are given in Table 1-3. These tables relate to the first example.

TABLE 1-1

| Selectable Parameter (references according to the Figure) | Value | Unit |
| --- | --- | --- |
| Working Volume of Activation Stage (1) | 80 | liter (l) |
| Working Volume of Production Stage (2) | 400 | liter (l) |
| Added Substrate (8a) | 7.2 | kg |
| Added Substrate (8b) | 44.0 | kg |
| Production Stage Output (16) | 6.15 | l/h (liter/hour) |
| Activation Stage Output (15) | 8 | l/h (liter/hour) |
| Permeate Stream From Activation Stage (13) | 20 | l/h (liter/hour) |
| Permeate Stream From Production Stage (14) | 173 | l/h (liter/hour) |
| Concentrate Stream From Activation Stage (11) | 2 | $m^3/h$ |
| Concentrate Stream From Production Stage (12') | 7 | $m^3/h$ |
| Temperature of Activation Stage (1) | 30 | °C. |
| Temperature of Production Stage (2) | 35 | °C. |
| pH Value of Activation Stage (1) | 4.5 | — |
| pH Value of Production Stage (2) | 4.8 | — |
| Oxygen Partial Pressure of Activation Stage (1) | 3.0 | % |
| Oxygen Partial Pressure of Production Stage (2) | 1.0 | % |

TABLE 1-2

| Resultant Parameters (reference according to the Figure) | Value | Unit |
| --- | --- | --- |
| Biomass Concentration in Activation Stage (1) | 50 | g YDS/l |
| Biomass Concentration in Production Stage (2) | 110 | g YDS/l |
| Average Cell Age | 65 | h |
| SNSDS in Activation Stage (1) | 6.5 | % |
| SNSDS in Production Stage (2) | 10.5 | % |
| Electrical Conductivity in Activation Stage (1) | 30 | mS/cm |
| Electrical Conductivity in Production Stage (2) | 50 | mS/cm |
| Osmotic Pressure in Activation Stage (1) (measured without ethanol) | 19 | bar |
| Osmotic Pressure in Production Stage (2) (measured without ethanol) | 30 | bar |
| Ethanol in Activation Stage (1) | 4.0 | Vol. % |
| Ethanol in Production Stage (2) | 6.8 | Vol. % |
| Growth Rate in Activation Stage (1) | 0.1 | l/h (liter/hour) |

TABLE 1-2-continued

| Resultant Parameters (reference according to the Figure) | Value | Unit |
|---|---|---|
| Growth Rate in Production Stage (2) | 0.006 | l/h (liter/hour) |
| Cell Activity in Activation Stage (1) | 88 | % |
| Cell Activity in Production Stage (2) | 80 | % |
| SDS in Activation Stage (1) | 3 | g/l (grams/liter) |
| SDS in Production Stage (2) | 3 | g/l (grams/liter) |

YDS = Yeast Dry Solids
SNSDS = Soluble Non-Sugar Dry Solids
SDS = Sugar Dry Solids

TABLE 1-3

| Process Quantities | Value | Unit |
|---|---|---|
| Product Formation in Entire System (including air venting losses) | 12.9 | l/h (liter/hour) |
| Yield (Theoretical) (without cell mass formation) | 99.0 | % |
| Yield (Theoretical) (including cell mass formation) | 93.3 | % |
| Product Formation Rate (for active total biomass) | 0.265 | gETOH/gYDS · h |
| Volume/Time Yield (with respect to Product Fermenter (2)) | 31.9 | lETOH/m$^3$ · h |

It was determined that once the parameters given in Tables 1-1, 1-2, and 1-3 were established in the system, they remained unchanged even after several hundred hours of continuous operation of the system. The exceptionally high volume/time yield of 31.9 liters of ethanol per m$^3$ per hour (lETOH/m$^3$·h) for the molasses raw material and ethanol concentrations of 6.8 Vol.% in the final product can only be achieved by the process of the present invention described herein. Any growth or increase of an infection or contamination is prevented by the appropriate control and adjustment of the medium conditions as described herein. A high degree of activity is maintained in the cell mass by supplying fresh biomass from the activation stage 1 into the production stage 2.

EXAMPLE 2

This example shows the achievement of a very high volume/time yield for a similarly high ethanol product concentration while using a special temperature-tolerant and osmo-tolerant yeast stock. The yeast stock used was the yeast HETT 80 deposited at the Institut fuer Gaerungsgewerbe, at 1000 Berlin 65, Federal Republic of Germany.

The culture growth was carried out in a manner similar to that described above in Example 1 with the parameters appropriately modified corresponding to the special yeast stock.

This special yeast stock exhibits a high temperature tolerance as well as a marked or pronounced tolerance for the end product alcohol, whereby higher product formation rates can be achieved even under difficult medium conditions. However, the expectable and achievable growth rates under these conditions are quite small so that in order to achieve the required average cell age, it is necessary to return some of tte biomass from the production stage 2 back into the activation stage 1. This is achieved through direct transfer of a portion 17 of the biomass retaining concentrate stream 12 from the production stage 2 back into the activation stage 1.

The selected and resultant parameters and the process quantities for Example 2 are given in Tables 2-1, 2-2, and 2-3.

TABLE 2-1

| Selectable Parameter (reference according to the Figure) | Value | Unit |
|---|---|---|
| Working volume of Activation Stage (1) | 80 | l (liter) |
| Working Volume of Production Stage (2) | 400 | l (liter) |
| Added Substrate (8a) | 7.2 | kg |
| Added Substrate (8b) | 60 | kg |
| Production Stage Output (16) | 6.23 | l/h (liter/hour) |
| Activation Stage Output (15) | 80 | l/h (liter/hour) |
| Production Stage Return Flow (17) | 32.7 | l/h (liter/hour) |
| Permeate Stream (13) From Activation Stage | 10 | l/h (liter/hour) |
| Permeate Stream (14) From Production Stage | 270 | l/h (liter/hour) |
| Concentrate Stream (11) From Activation Stage | 2 | m$^3$/h |
| Concentrate Stream (12) From Production Stage | 7 | m$^3$/h |
| Temperature of Activation Stage (1) | 32 | °C. |
| Temperature of Production Stage (2) | 37 | °C. |
| pH-Value of Activation Stage (1) | 4.5 | — |
| pH-Value of Production Stage (2) | 5.0 | — |
| Oxygen Partial Pressure of Activation Stage (1) | 3.0 | % |
| Oxygen Partial Pressure of Production Stage (2) | 1.0 | % |

TABLE 2-2

| Resultant Parameters (references according to the Figure) | Value | Unit |
|---|---|---|
| Biomass Concentration in Activation Stage (1) | 50 | g YDS/l |
| Biomass Concentration in Production Stage (2) | 110 | g YDS/l |
| Average Cell Age | 70 | h |
| SNSDS in Activation Stage (1) | 6.0 | % |
| SNSDS in Production Stage (2) | 10.0 | % |
| Electrical Conductivity in Activation Stage (1) | 26 | mS/cm |
| Electrical Conductivity in Production Stage (2) | 46 | mS/cm |
| Osmotic Pressure in Activation Stage (1) (measured without ethanol) | 16 | bar |
| Osmotic Pressure in Production Stage (2) (measured without ethanol) | 29 | bar |
| Ethanol in Activation Stage (1) | 3.8 | Vol. % |
| Ethanol in Production Stage (2) | 6.0 | Vol. % |
| Growth Rate in Activation Stage (1) | 0.1 | l/h (liter/hour) |
| Growth Rate in Production Stage (2) | 0.0064 | l/h (liter/hour) |
| Cell Activity in Activation Stage (1) | 90 | % |
| Cell Activity in Production Stage (2) | 85 | % |
| SDS in Activation Stage (1) | 3 | g/l (grams/liter) |

TABLE 2-2-continued

| Resultant Parameters (references according to the Figure) | Value | Unit |
| --- | --- | --- |
| SDS in Production Stage (2) | 3 | g/l (grams/liter) |

YDS = Yeast Dry Solids
SNSDS = Soluble Non-Sugar Dry Solids
SDS = Sugar Dry Solids

TABLE 2-3

| Method Quantities | Value | Unit |
| --- | --- | --- |
| Product Formation In Entire System (including air venting losses) | 17.2 | l/h (liter/hour) |
| Yield (Theoretical) (without cell mass formation) | 99.5 | % |
| Yield (Theoretical) (with cell mass formation) | 94.8 | % |
| Product Formation Rate (for active total biomass) | 0.336 | gETOH/gYDS · h |
| Volume/Time Yield (with respect to production fermenter (2)) | 43 | lETOH/$m^3$ · h |

An improved product formation rate of 0.336 grams of ethanol per gram of yeast dry solids per hour (0.336 gETOH/gYDS·h) compared to that of Example 1 is achieved because of the lower final product concentration of 6.0 Vol.% ethanol and because of the use of the special yeast stock HETT 80. This increased product formation rate lead to an increase in the volume per time yield of 43 liters of ethanol per cubic meter per hour (43 l ETOH/$m^3$·h). The necessary cell activity and a corresponding growth of this yeast is achieved through reducing the average residence time of the biomass in the production stage 2 by returning a partial stream 17 of biomass containing medium from the production stage 2 back into the activation stage 1.

Although the invention has been described with reference to specific example embodiments, it will be appreciated, that it is intended to cover all modifications and equivalents within the scope of the appended claims.

What I claim is:

1. A process for the continuous production in a two stage fermenter system of low aliphatic alcohols or organic solvent products, from sugar containing substances providing a raw material substrate quantity, comprising the following steps,
    (a) supplying about 5 to 20% of said substrate quantity into a first activating fermentation stage and supplying about 95 to 80% of said substrate quantity into a second production fermentation stage,
    (b) introducing an oxygen suppying gas into both stages in quantities sufficient to adjust an oxygen partial pressure in said first stage at approximately 3% and an oxygen partial pressure in said second stage at approximately 1%,
    (c) maintaining a temperature within the range of about 30° C. to 35° C. in said first stage and a temperature of about 35° C. to 40° C. in said second stage,
    (d) passing a portion of an output flow from said first stage through first microfilter means (3) to produce a first concentrate and a first permeate and feeding said first permeate and the remainder of said output flow into said second stage,
    (e) passing an output flow from said second stage through second microfilter means (4) to produce a second concentrate and a second permeate, back-feeding a portion of said second concentrate partially into said second stage (at 12') while removing another portion of said second concentrate (at 16) from said system as a product stream, and removing said second permeate from said system (at 14),
    (f) adjusting said feeding of said first permeate and of said remainder from said first stage into said second stage, said back-feeding of said second concentrate, and said removing of said other portion of said second concentrate and of said second permeate in such a manner, that the following conditions are satisfied: cell mass residence times in said first stage are within the range of about 0.5 to about 2.0 hours, cell mass residence times in said second stage are within the range of about 5 to about 15 hours, and an average cell age is within the range of about 40 to about 100 hours, and
    (g) using for said first stage a fermenter having a given volume and using for said second stage a fermenter having a volume about five times to about ten times said given volume of said first stage fermenter, whereby said first stage is operated as a non-sterile activating stage for substantially promoting cell growth and activation while said second stage is operated as a non-sterile producing stage.

2. The process of claim 1, further comprising returning (at 17) a third portion of said second concentrate from said second stage to said first stage while maintaining said conditions of step (f).

3. The process of claim 1, supplying a microorganism to said first and second stages in such quantities that in said first stage a microorganism concentration of less than 80 grams dry substance per liter and a microorganism concentration of more than 80 grams dry substance per liter in said second stage are maintained.

4. The process of claim 1, wherein nutrient and growth promoting substances for said microorganisms are supplied only into said first stage.

5. The process of claim 1, wherein microorganisms are supplied directly into said first stage and into said second stage as a preliminary start-up step in such a way that said second stage is operational well prior to said first stage.

6. A process for the continuous fermentative production of low aliphatic alcohols or organic solvents, from sugar containing substrates, comprising:
    (a) supplying a first substrate quantity of 5 to 20% of a total substrate quantity into a first activation fermentation stage;
    (b) supplying a second substrate quantity of 95 to 80% of said total substrate quantity into a second production fermentation stage;
    (c) suppyling process water into both stages and nutrient and growth substances only into the first stage in sufficient quantities to establish a total material volume ratio of the first stage to the second stage between 1:10 and 1:5;
    (d) supplying a first quantity of an oxygen suppyling gas to said first stage to establish an oxygen partial pressure of approximately 3% in said first stage,
    (e) supplying a second quantity, which is a fraction of said first quantity, of an oxygen suppyling gas to said second stage to establish an oxygen partial pressure of approximately 1% in said second stage;

(f) controlling the temperature of said first stage to between 30° and 35° C.;

(g) controlling the temperature of said second stage to between 35° and 40° C.;

(h) introducing a microorganism to said first stage, to subject said first substrate quantity to the effects of said microorganism in an unsterile process, to include a large cell growth or cell activation rate in said first activation stage;

(i) introducing said microorganism also to said second stage, to subject said second substrate quantity to the effects of said microorganism in an unsterile process, to induce a high product formation rate in said second production stage;

(j) passing a first partial outflow from said first stage through a first microfilter (3) to form a first microfiltered permeate stream (at 13) and a first concentrate (at 11);

(k) discharging a second partial outlet flow (at 15) from said first stage;

(l) directing said first microfiltered permeate stream (at 13) and said second partial outlet flow (at 15) into said second stage;

(m) passing a third outlet flow from said second stage through a second microfilter (4) to form a second microfiltered permeate stream and a second concentrate stream retained by said microfiltering;

(n) discharging said second permeate stream as a first output stream (at 14), and discharging at least a portion of said second concentrate stream as a second output stream (at 16);

(o) feeding-back at least a portion of said second concentrate stream to said second stage (at 12'); and (p) controlling the flow rates of said first permeate stream (at 13), said second partial outlet flow (at 15), said first output stream (at 14), said second output stream (at 16), and said second stage return portion (at 12') of said second concentrate stream, so that for a residence time of said microorganism of 0.5 to 2.0 hours in said first stage and of 5 to 15 hours in said second stage, an average cell age of said microorganism of 40 to 100 hours is established and maintained.

7. The process of claim 6, wherein said substrate quantities are volume percentages of the total substrate volume.

8. The process of claim 1, wherein said low aliphatic alcohol is ethanol.

9. The process of claim 6, wherein said low aliphatic alcohol is ethanol.

* * * * *

UNITED STATES PATENT AND TRADEMARK OFFICE
CERTIFICATE OF CORRECTION

PATENT NO. : 4,845,033
DATED : July 4, 1989
INVENTOR(S) : Uwe Tegtmeier

It is certified that error appears in the above-identified patent and that said Letters Patent is hereby corrected as shown below:

Claim 6, (Col. 12, line 59), replace "suppyling" by --supplying--;

(Col. 12, line 64), replace "suppyling" by --supplying--;

(Col. 13, lines 9 and 10), replace "include" by --induce--.

Signed and Sealed this

Twenty-seventh Day of February, 1990

Attest:

JEFFREY M. SAMUELS

Attesting Officer

Acting Commissioner of Patents and Trademarks